US011682502B2

(12) United States Patent
Kim et al.

(10) Patent No.: US 11,682,502 B2
(45) Date of Patent: Jun. 20, 2023

(54) METHOD OF FABRICATING SUSPENDED NANOWIRE USING HEAT TREATMENT

(71) Applicant: Industry-Academic Cooperation Foundation, Yonsei University, Seoul (KR)

(72) Inventors: Jongbaeg Kim, Goyang-si (KR); Yongkeun Oh, Anyang-si (KR); Dae-Sung Kwon, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 455 days.

(21) Appl. No.: 16/885,802

(22) Filed: May 28, 2020

(65) Prior Publication Data

US 2020/0381144 A1 Dec. 3, 2020

(30) Foreign Application Priority Data

May 28, 2019 (KR) .......................... 10-2019-0062617

(51) Int. Cl.
*H01B 13/00* (2006.01)
*D01D 5/00* (2006.01)
(Continued)

(52) U.S. Cl.
CPC ....... *H01B 13/0016* (2013.01); *D01D 5/0007* (2013.01); *D01D 10/02* (2013.01); *G01N 27/121* (2013.01); *G01P 15/122* (2013.01); *H01B 1/12* (2013.01); *B82Y 30/00* (2013.01); *B82Y 40/00* (2013.01); *G01N 33/005* (2013.01); *G01N 33/0037* (2013.01)

(58) Field of Classification Search
CPC .... H01B 13/0016; H01B 1/12; D01D 5/0007; D01D 10/02; D01D 11/06; D01D 5/003; D01D 5/0076; G01N 27/121; G01N 33/0037; G01N 33/005; G01N 27/126; G01N 27/127; G01P 15/122; B82Y 30/00; B82Y 40/00; B82Y 15/00; D01F 11/00; Y02A 50/20; B81C 1/00095; B81C 2203/033
See application file for complete search history.

(56) References Cited

U.S. PATENT DOCUMENTS 9,513,555 B2 * 12/2016 Shin .......................... G03F 7/40
10,737,938 B2 * 8/2020 Sam ....................... C25D 13/22
(Continued)

OTHER PUBLICATIONS

Y. Oh, D.-S. Kwon, W. Kim and J. Kim, "Location-specific fabrication of suspended metal nanowire based on electrospun nanofibers on MEMS platform," 2018 IEEE Micro Electro Mechanical Systems (MEMS), 2018, pp. 494-497, doi: 10.1109/MEMSYS.2018.8346597. (Year: 2018).*
(Continued)

*Primary Examiner* — Jonathan Han
(74) *Attorney, Agent, or Firm* — Paratus Law Group, PLLC

(57) ABSTRACT

A method of fabricating a polymer wire according to the present embodiment includes preparing an electrode platform having a micro gap, forming a plurality of single polymer wires on the electrode platform, and a heat treatment operation of aggregating the plurality of single polymer wires to form an aggregated polymer wire.

15 Claims, 17 Drawing Sheets

(51) Int. Cl.
*G01N 27/12* (2006.01)
*G01P 15/12* (2006.01)
*D01D 10/02* (2006.01)
*B82Y 40/00* (2011.01)
*B82Y 30/00* (2011.01)
*H01B 1/12* (2006.01)
*G01N 33/00* (2006.01)

(56) References Cited

U.S. PATENT DOCUMENTS

2008/0224123 A1* 9/2008 Martin ................ H01L 29/0665
257/23
2018/0015201 A1* 1/2018 Fong .................... D04H 1/4242

OTHER PUBLICATIONS

Seung-Hoon Choi et al., "Hollow ZnO Nanofibers Fabricated Using Electrospun Polymer Templates and Their Electronic Transport Properties", ACS NANO, Aug. 17, 2009, vol. 3, No. 9, pp. 2623-2631.

* cited by examiner

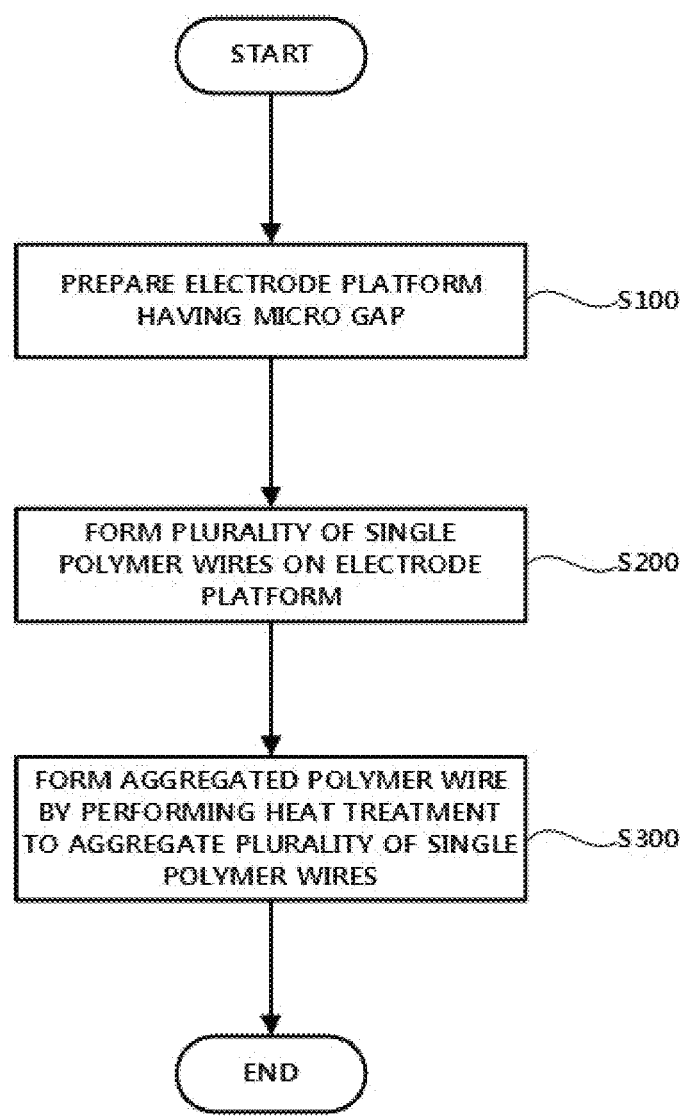

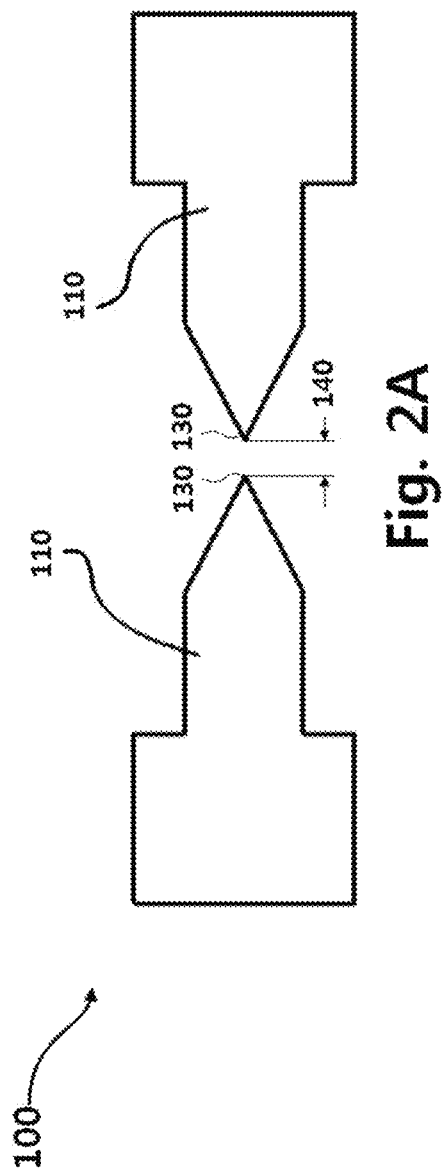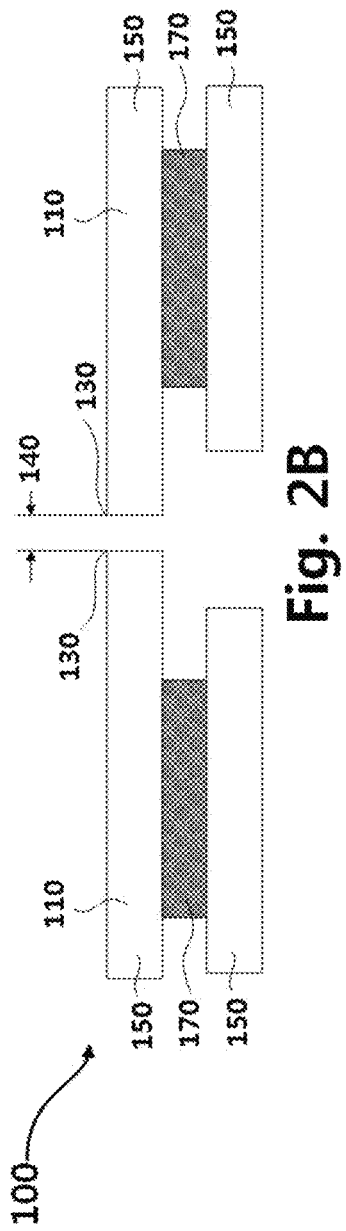

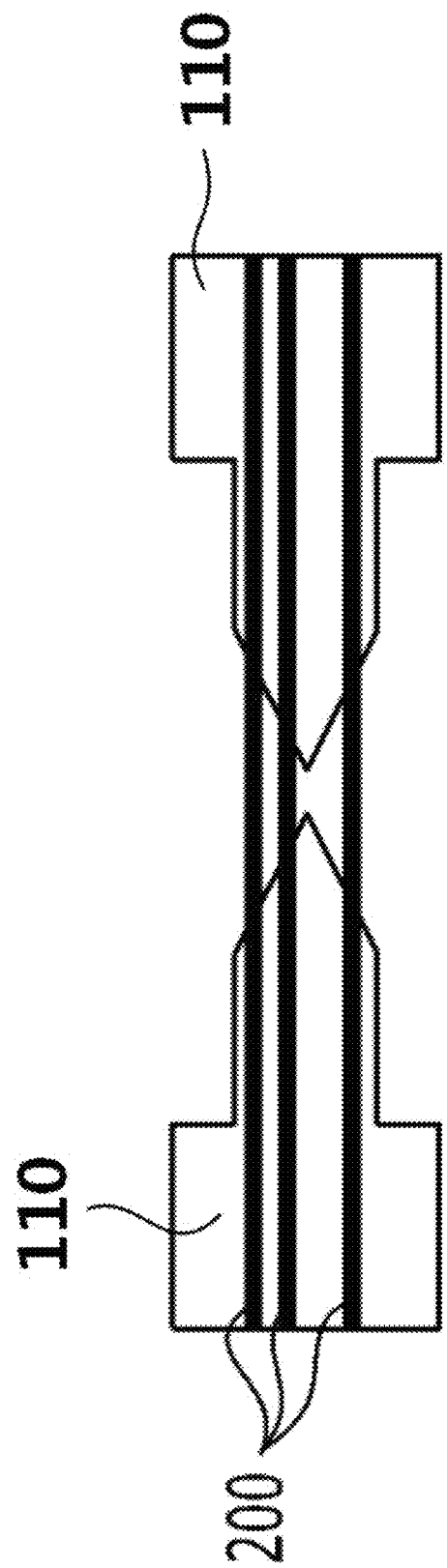

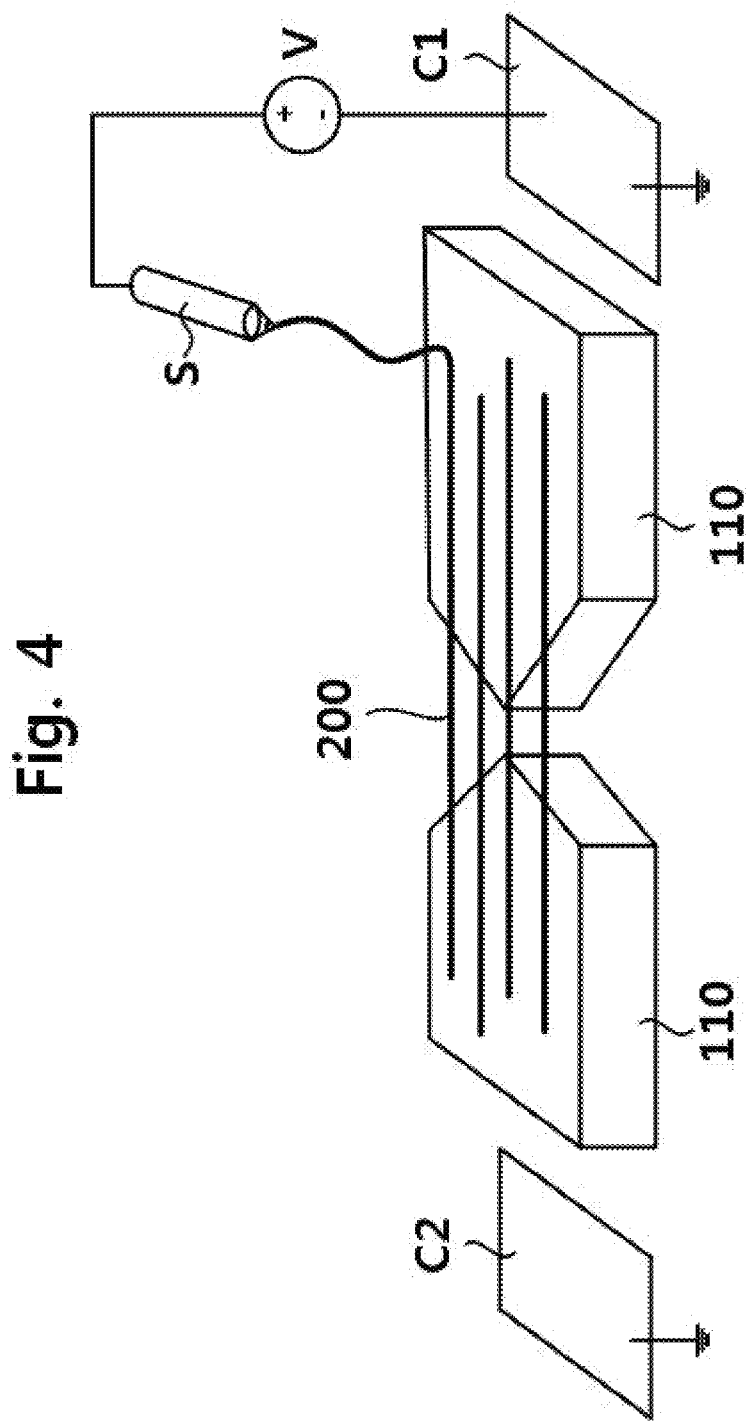

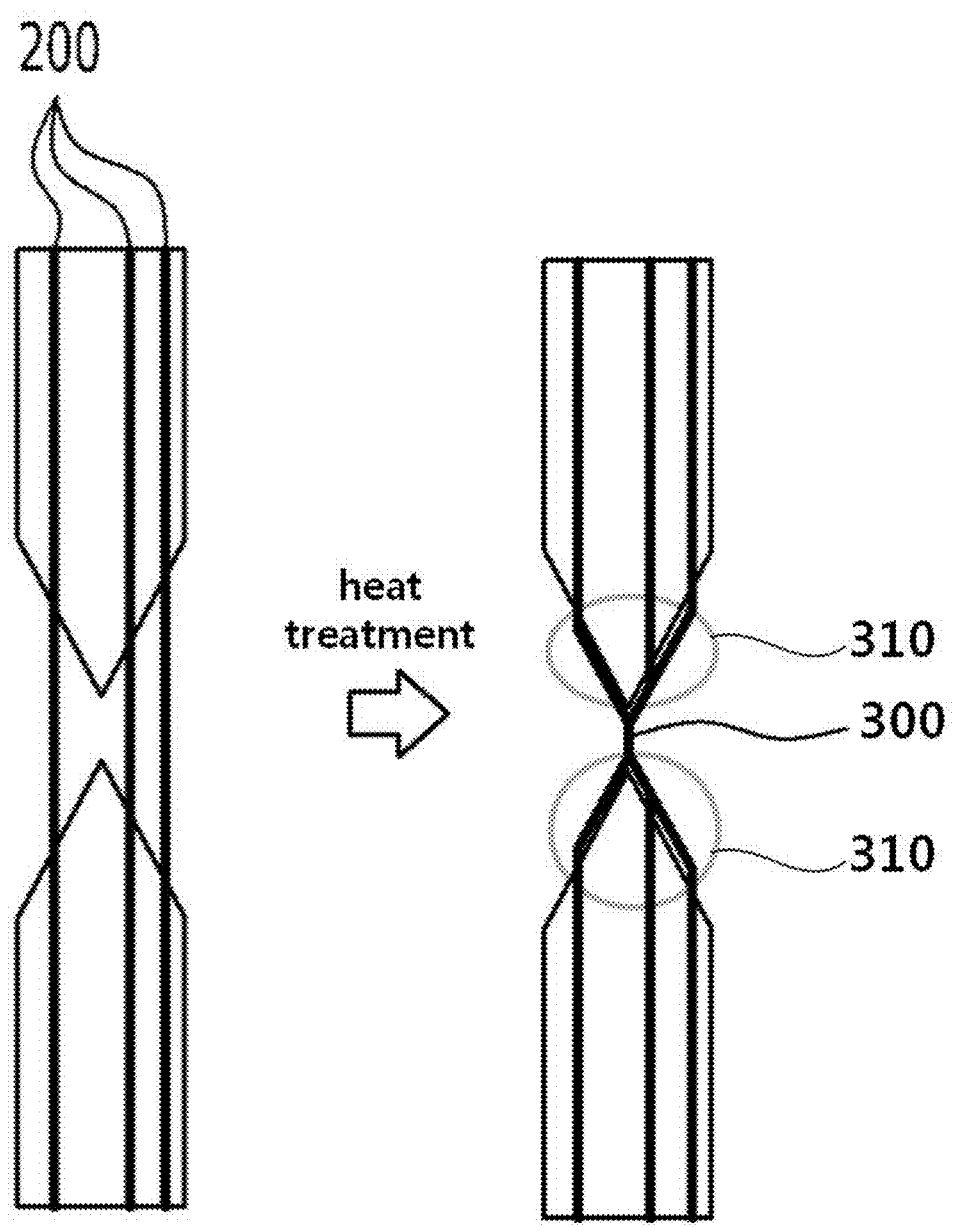

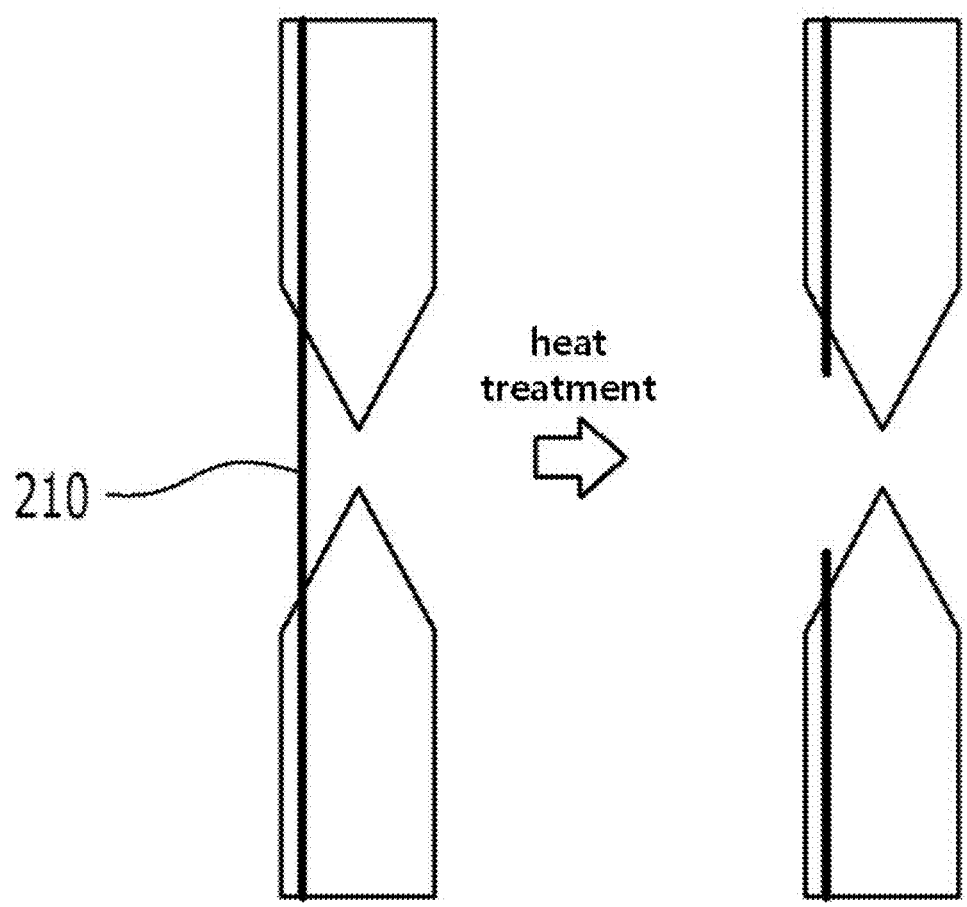

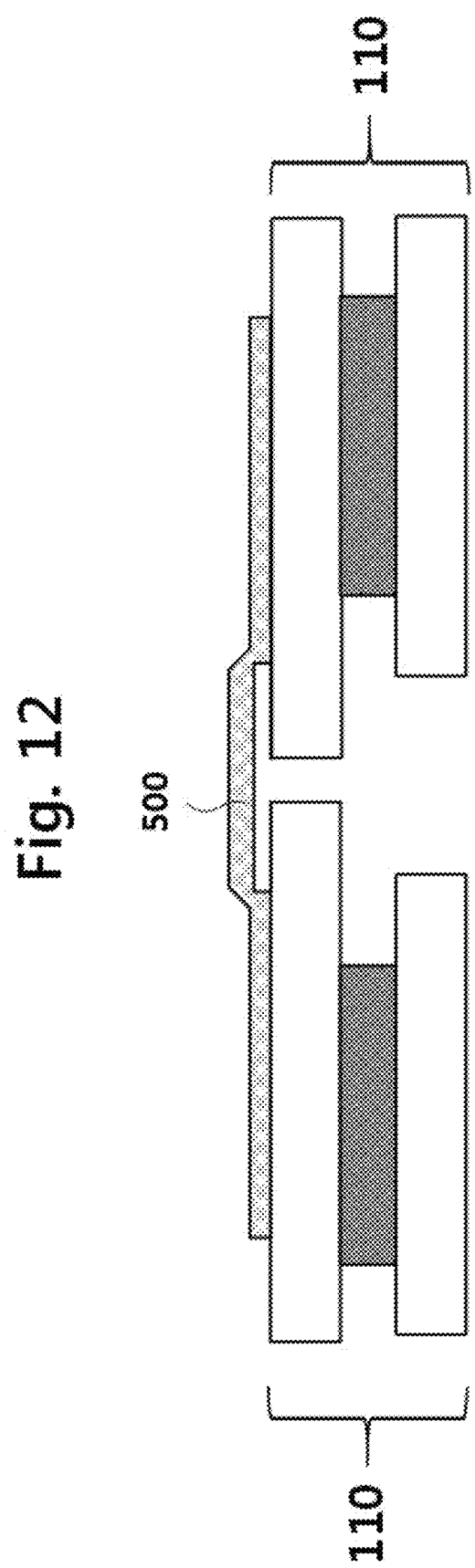

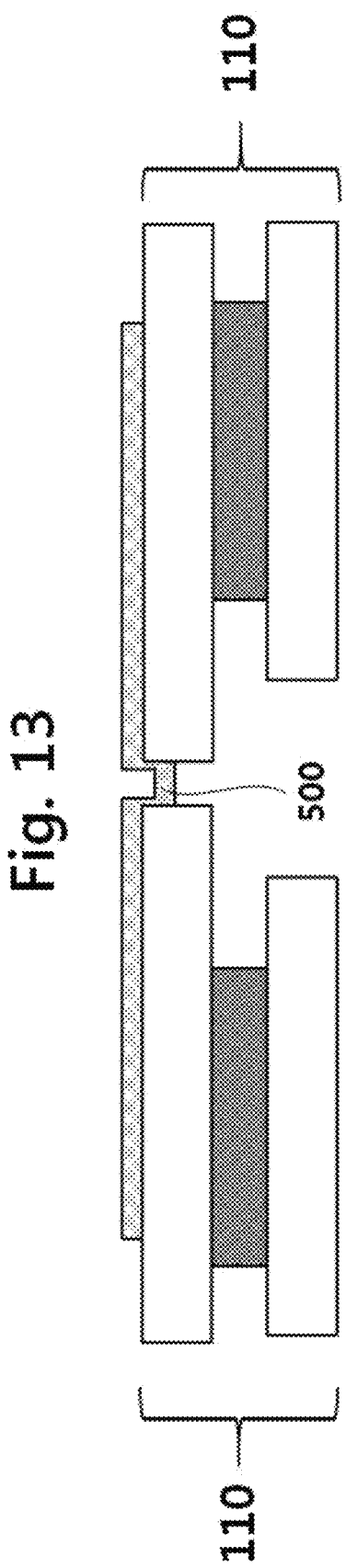

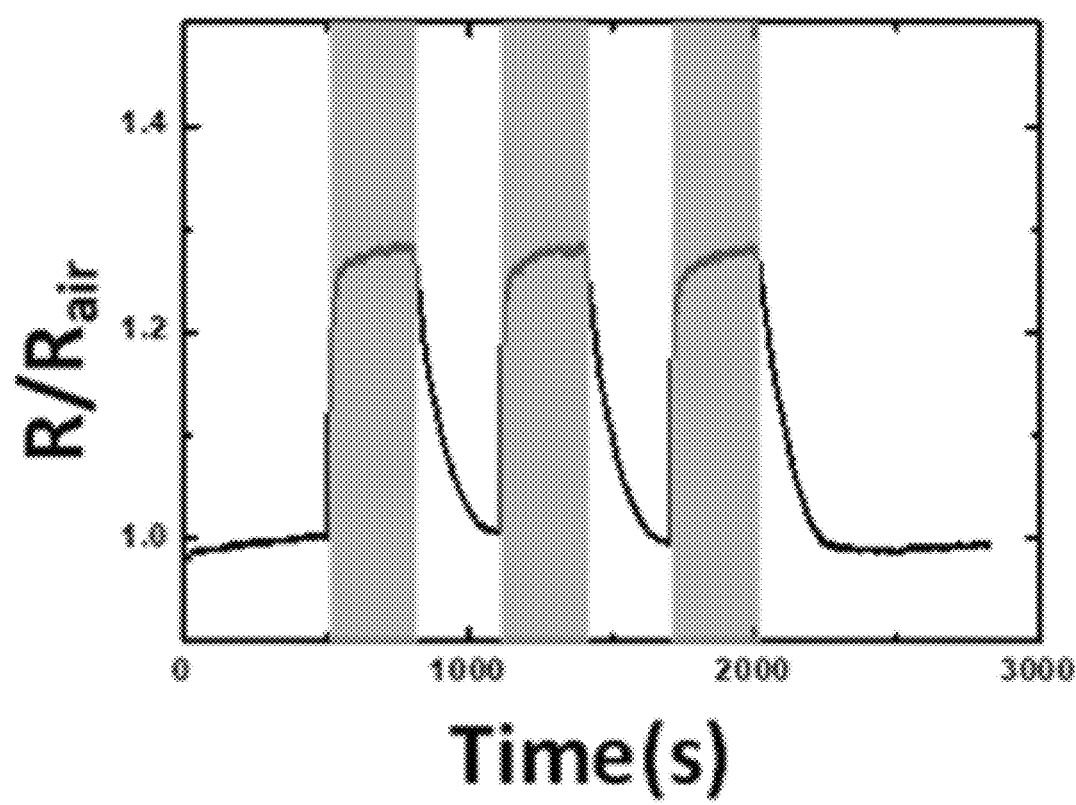

METHOD OF FABRICATING SUSPENDED NANOWIRE USING HEAT TREATMENT

CROSS-REFERENCE TO RELATED APPLICATION

This application claims priority to and the benefit of Korean Patent Application No. 10-2019-0062617, filed on May 28, 2019, the disclosure of which is incorporated herein by reference in its entirety.

BACKGROUND

1. Field of the Invention

The present disclosure relates to a method of fabricating a suspended nanowire using heat treatment, and more particularly, to a method of fabricating a suspended nanowire, a position of the nanowires and number of the nanowires are adjustable using a microelectromechanical systems (MEMS) platform and heat treatment.

2. Discussion of Related Art

Nanowires are widely used in gas sensors, biosensors, catalysts, and the like due to the intrinsic properties of materials thereof such as a great surface area relative to the volume and expression at a small size. When such nanowires are attached to a substrate, the temperature of the nanowires is greatly affected by the thermal conductivity of the substrate, and when current flows, unnecessary interference such as parasitic capacitance may be generated around the nanowires. Accordingly, it is advantageous to fabricate the nanowires in a suspended structure in order to fully utilize the intrinsic properties of the nanowires.

In addition, the shape and number of the nanowires directly affect the performance of a device such as a gas sensor or the like, and thus it is necessary to control the number of the nanowires to be formed or the positions in which the nanowires are formed.

Conventional nanowire fabrication methods include a vapor-liquid-solid (VLS) growth method, a chemical vapor deposition (CVD) method, a sol-gel processing method, a laser pyrolysis method, an atomic or molecular condensation method, a layer-by-layer self-assembly method, a molecular self-assembly method, and the like as a bottom-up method and include an X-ray lithography method, an ion-beam lithography method, a printing and imprinting method, and the like as a top-down method.

These conventional methods are planar techniques, and thus it is difficult to produce three-dimensional nanowires (such as suspended nanowires) of a desired shape, and in the conventional methods, due to the high temperature process, the cost is increased, and materials capable of fabricating nanowires are limited.

Meanwhile, in a more recent nanowire fabricating method, there is a method of fabricating nanowires using electrospinning, and this includes fabricating metal oxide nanowires using sintering or calcinations and fabricating nanowires by coating different materials on a polymer template.

SUMMARY

A conventional method of fabricating suspended nanowires may produce suspended nanowires but has disadvantages that materials used are limited, the positions in which the nanowires are formed may not be controlled, or it is difficult to fabricate the nanowires in batch.

The present disclosure is directed to solving problems of the related art. The present disclosure is also directed to providing a method that capable of forming a large area and amount of nanowires of a controlled positions and number using batch fabrication process.

The present disclosure is also directed to providing a sensor formed by the method described above.

According to an aspect of the present disclosure, there is provided a method of fabricating a polymer wire including preparing an electrode platform having a micro gap, forming a plurality of single polymer wires on the electrode platform, and a heat treatment operation of aggregating the plurality of single polymer wires to form an aggregated polymer wire.

According to another aspect of the present disclosure, there is provided a method of fabricating a metal material wire including preparing an electrode platform having a micro gap, forming a plurality of single polymer wires on the electrode platform, a heat treatment operation of aggregating the plurality of single polymer wires to form an aggregated polymer wire, coating the aggregated polymer wire with a metal material, and removing the aggregated polymer wire to form the metal material wire.

According to still another aspect of the present disclosure, there is provided a wire connected between protruding tips of two electrodes, each having the protruding tip and disposed such that the tips face each other, wherein the wire is connected to each of the electrodes through one or more branches formed on an outer periphery of the tip.

According to yet another aspect of the present disclosure, there is provided a sensor including two electrodes each having a protruding tip, and wire segments located on surfaces of the two electrodes, respectively and extending through the protruding tips, wherein one or more of the two electrodes are movable, and an electrical property between the wire segments changes as one or more of the two electrodes move.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which:

FIG. 1 is a flowchart schematically illustrating a method of fabricating polymer wires according to the present embodiment;

FIG. 2A is a plan view of an electrode platform having a micro gap, and FIG. 2B is a cross-sectional view of the electrode platform in FIG. 2A;

FIG. 3 is a plan view schematically illustrating the state in which a plurality of single polymer wires are formed on the electrode platform;

FIG. 4 is a view schematically illustrating an operation of forming single polymer wires using electrospinning;

FIGS. 5 to 7 are views each illustrating an example of a heat treatment process;

FIG. 12 is a cross-sectional view schematically illustrating the state in which the aggregated polymer wire is removed from the aggregated polymer wire coated with the metal material;

FIG. 13 is a cross-sectional view illustrating the state in which a drying process is performed after the aggregated polymer wire is removed from the aggregated polymer wire coated with the metal material;

FIG. 16 is a graph illustrating the results of detecting hydrogen gas by a sensor using the palladium wire according to the present embodiment.

DETAILED DESCRIPTION

Figure 7:
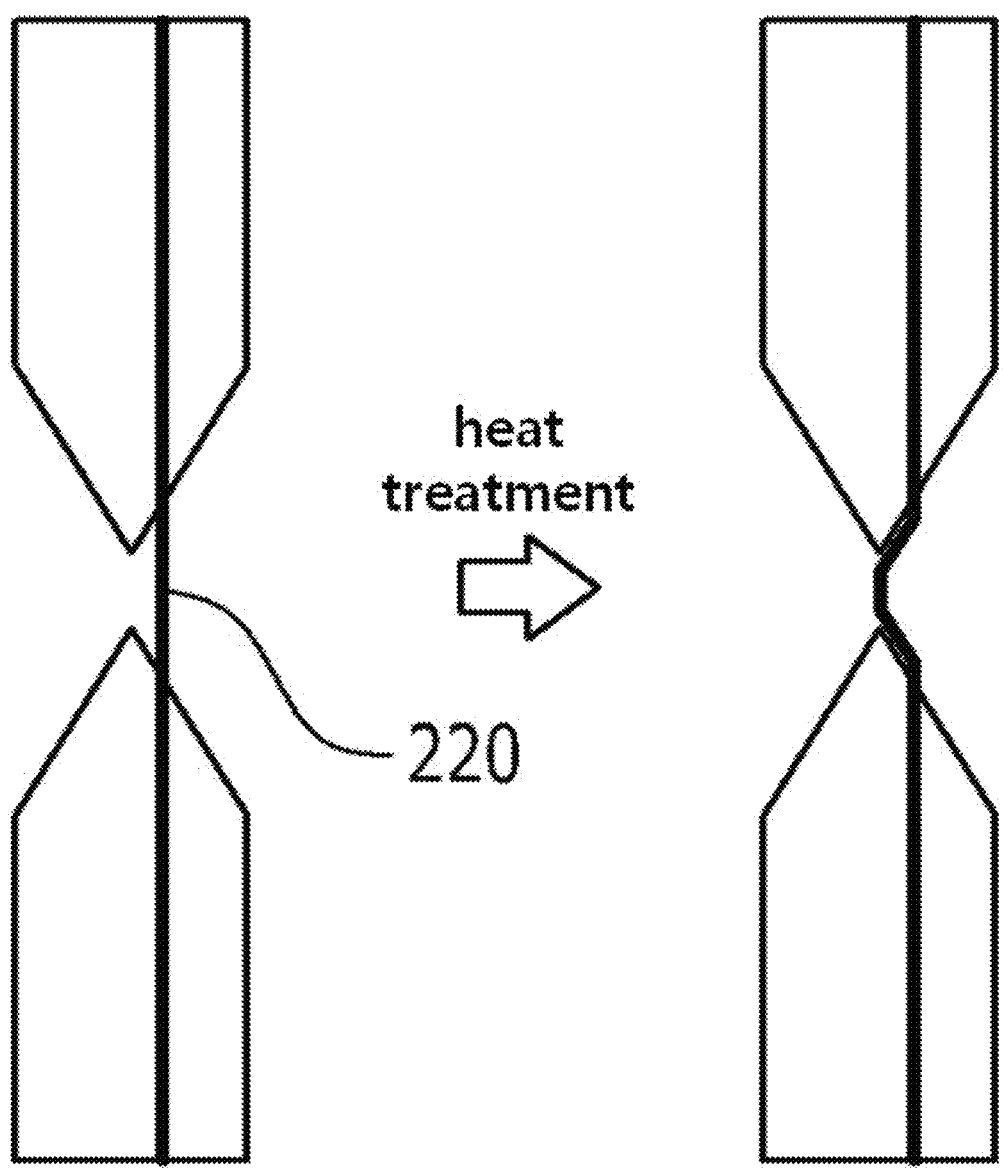

Hereinafter, embodiments of the present disclosure will be described in detail with reference to the accompanying drawings. It will be apparent to those skilled in the art that these embodiments are provided by way of example only to describe the present disclosure in more detail, and the scope of the present disclosure is not limited by these embodiments.

Further, it should be noted that the terms or words used in the present specification and the claims should not be construed as being limited to general and dictionary meanings but should be interpreted based on the meanings and concepts corresponding to technical aspects of the present disclosure.

Parts irrelevant to the description will be omitted in the drawings in order to clearly describe the proposed disclosure. Similar parts are denoted by similar reference numerals throughout the specification. In addition, unless otherwise specifically stated, when a part is referred to as "including" an element, this may further include one or more other elements but does not preclude the presence of one or more other elements.

FIG. 1 is a flowchart schematically illustrating a method of fabricating polymer wires according to the present embodiment. Referring to FIG. 1, the method of fabricating the polymer wires according to the present embodiment includes preparing an electrode platform having a micro gap (S100), forming a plurality of single polymer wires in the electrode platform (S200), and a heat treatment operation of forming an aggregated polymer wire by aggregating the plurality of single polymer wires (S300). The method of fabricating the polymer nanowires according to the present embodiment is provided with the advantage that the entire process is performed as a batch process so that manufacturing costs may be reduced.

In the followings, the term "micro gap" refers to the gap between the electrode and the electrode, and is denoted as a "micro gap," but the distance of the gap may have a nanometer or millimeter unit, and of course, may have a micrometer unit.

Hereinafter, the method of fabricating the polymer wires according to the present embodiment will be described with reference to the accompanying drawings. An electrode platform 100 having a micro gap 140 is prepared (S100). FIG. 2A is a plan view of the electrode platform 100 having the micro gap 140, and FIG. 2B is a cross-sectional view of the electrode platform 100 in FIG. 2A. Referring to FIGS. 2A and 2B, the electrode platform 100 may be formed using a silicon-on-insulator (SOI) wafer. As an example, the electrode platform 100 may be a structure in which an insulating layer 170 containing silicon oxide is disposed between silicon layers 150, and may be fabricated using an SOI wafer.

In an embodiment that is not illustrated, a metal film may be formed on surfaces of electrodes 110 included in the electrode platform 100. As an example, the metal film may be a metal having a high electrical conductivity and may be one of gold (Au), silver (Ag), and platinum (Pt). The metal thin film formed on the surface of the electrode 110 may allow the detection properties of a sensor including the wires that is formed according to the present embodiment to be limited to changes occurring in nanowires.

The electrodes 110 may each have a tip 130 having a pointed shape, and the electrodes 110 may be disposed such that the tips 130 face each other. The electrodes 110 are spaced apart from each other by as much as the micro gap 140. As an example, the micro gap 140 between the tips 130 of the electrodes may be in a range of one hundred nanometers to several hundred micrometers. In addition, the electrodes 110 may have a triangular shape.

The single polymer wires move to a position having a more stable state due to the subsequent heat treatment process (S300) so that the electrode 110 may include the tip 130 having a pointed shape as illustrated in the drawing.

A plurality of single polymer wires 200 are formed on the electrode platform 100 (S200). FIG. 3 is a plan view schematically illustrating the state in which the plurality of single polymer wires 200 are formed on the electrode platform 100. Referring to FIG. 3, in the operation of forming the single polymer wires 200, the plurality of single polymer wires 200 are formed on a surface of the electrode platform 100 such that the single polymer wires 200 are suspended across the micro gap 140.

FIG. 4 is a view schematically illustrating the operation of forming the single polymer wires 200 using electrospinning. Referring to FIG. 4, collector electrodes C1 and C2 are connected to reference voltage and may be located around the electrode platform 100. As an embodiment, the reference voltage may be a ground voltage. Two collector electrodes C1 and C2 may be used to align the single polymer wires 200. Voltage is provided to a discharge device S such as a syringe. For example, the voltage provided to the discharge device S may be in a range of 8 kV to 15 kV.

The voltage provided to the discharge device S is provided to a discharge nozzle configured to form the single polymer wires 200 by discharging a polymer solution, thereby charging the discharged polymer. The discharge nozzle discharges the polymer solution to form the single polymer wires 200, and the single polymer wires 200 are formed to be suspended across the micro gap 140. A diameter of the single polymer wires 200 formed as described above is not particularly limited, but may be about 100 to 1000 nm so that aggregation smoothly occurs.

A time for forming the single polymer wires 200 by discharging the polymer solution may be, as an example, 10 to 120 seconds. The polymer solution is used to form the single polymer wires 200 using an electrospinning method, and is not specifically limited as long as it is a polymer solution capable of forming the single polymer wires 200 by performing electrospinning. In one embodiment, the polymer solution may preferably include at least one selected from the group consisting of polyethylene oxide, polyurethane, polyethylene, polypropylene, polystyrene, polyvinyl chloride, and polybutadiene, and more preferably, may include polyethylene oxide.

The diameter of an aggregated polymer wire 300 to be formed may be adjusted by controlling the conditions of electrospinning (the time of the electrospinning, the voltage applied to the nozzle, the distance from nozzle to target, the solution to be electrospun). As the time for performing the electrospinning increases, the number of the single polymer wires 200 formed increases, and accordingly, the number of the single polymer wires 200 aggregated increases. Thus, the finally produced aggregated polymer wire 300 becomes thick. In addition, when the diameter of the single polymer wires 200 to be formed is increased by controlling the conditions of the electrospinning, the diameter of the finally produced aggregated polymer wire 300 is increased.

The single polymer wires 200 are aggregated by performing heat treatment to form the aggregated polymer wire 300 (S300). The heat treatment process may be performed by exposing the single polymer wires 200 to a temperature of 50° C. to 200° C. such that the single polymer wires 200 change to a glass transition state. As described above, the single polymer wires 200 change to the glass transition state due to the heat provided during the heat treatment process. The single polymer wires 200 changed to the glass transition state aggregate together to form the aggregated polymer nanowire.

FIGS. 5 to 7 are views each illustrating an example of the heat treatment process. Referring to FIG. 5, when heat is applied to the single polymer wires 200 formed on the electrode platform 100, the plurality of single polymer wires 200 change to a glass transition state and move to a central portion of the tip 130, which is a stable position.

Referring to FIG. 6, a single polymer wire 210 formed to be spaced apart from the central portion of the tip 130 is broken during movement. On the other hand, as shown in FIG. 7, a single polymer wire 220 formed at a distance close to the central portion of the tip 130 is not broken during the heat treatment process and moves to the central portion of the tip 130. A plurality of single polymer wires 220 located at the central portion and/or near the central portion of the tip 130 are aggregated into one to form the aggregated polymer wire 300 at the central portion of the tip 130 and form a plurality of branches 310 at the boundary of the tip.

Figure 8:
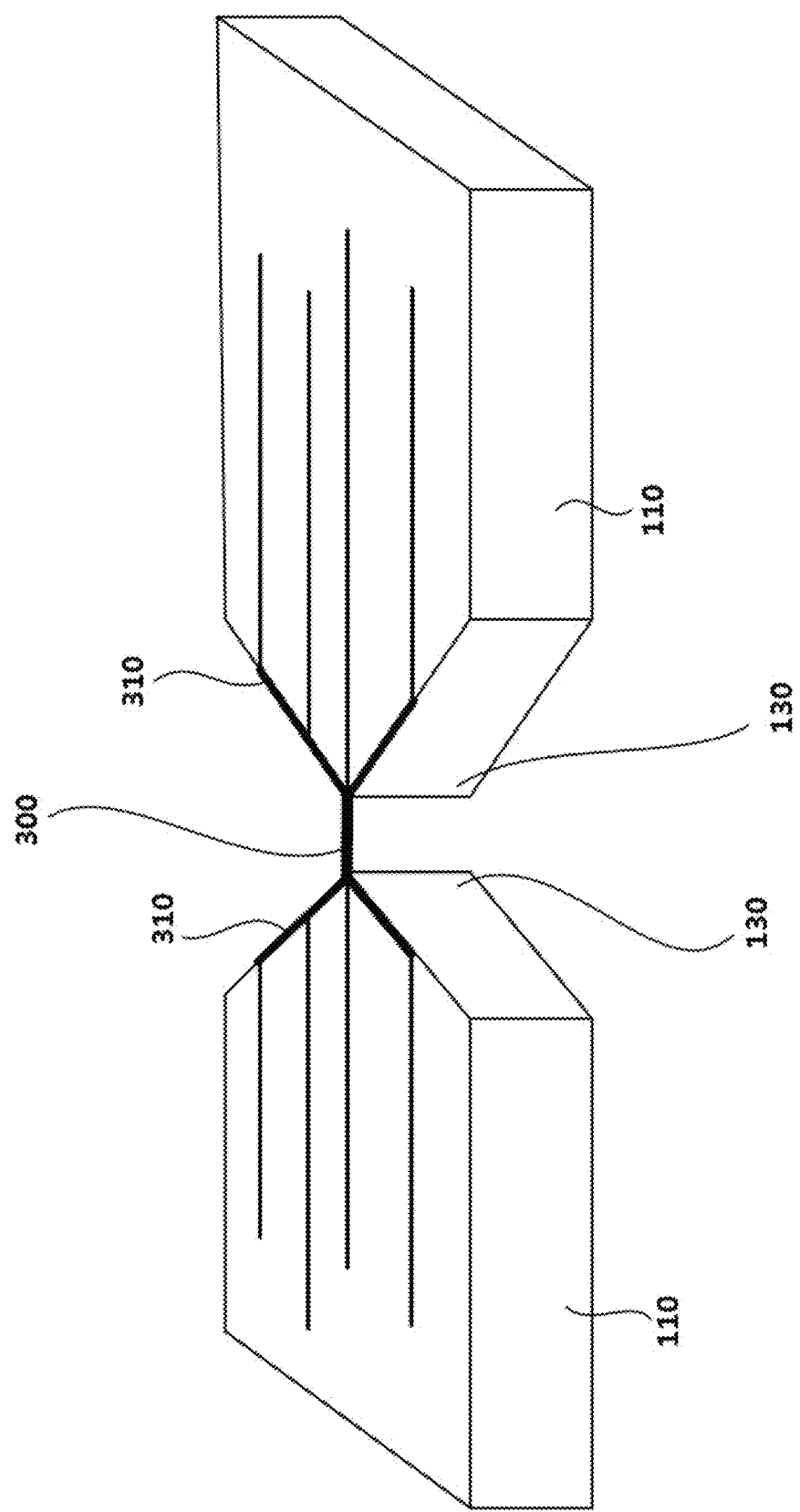
FIG. 8 is a view schematically illustrating the state in which the heat treatment process is completed.

FIG. 8 is a view schematically illustrating the state in which the heat treatment process is completed. Referring to FIG. 8, in the heat treatment process, the single polymer wires 200 that move to the central portion of the tip 130 are aggregated together as illustrated in the drawing to form the aggregated polymer wire 300. The aggregated polymer wire 300 is formed to be suspended between the tips 130 facing each other.

Further, the aggregated polymer wire 300 suspended between the tips 130 may be connected to the branches 310 formed along the outer periphery of the tip 130. In the example illustrated in FIG. 8, the aggregated polymer wire 300 may be connected to the plurality of branches 310 formed in left and right directions with respect to the tip. As another example, one branch 310 may be formed. When the single polymer wires 200 are formed only in one of the left direction or the right direction with respect to the tip, a single branch 310 may be formed. The branches 310 formed as described above enhance the adhesion between the aggregated polymer wire 300 and the tip 130.

The heat treatment operation (S300) may be performed by exposing the single polymer wires 200 to a temperature of 60 to 200° C. for 1 to 5 minutes. In one embodiment, the heat treatment operation (S300) may be performed using an oven. When the single polymer wires 200 are made of polyethylene oxide (PEO), the electrode platform 100 may be placed in the oven at 80° C. and heat-treated for about 1 minute to form the aggregated polymer wire 300.

In another embodiment, the electrode platform 100 on which the single polymer wires 200 are formed is placed on a hot plate at about 60° C. and heat-treated for about 3 to 5 minutes to form the aggregated polymer wire 300. The heat treatment conditions described above may vary depending on the material of the single polymer wires 200.

A structure including the aggregated polymer wire 300 formed as described above may be used as a humidity sensor. As an example, the aggregated polymer wire 300 may be formed of one or more among polypyrrole (PPy), PEDOT:PSS, and polyacetylene. These vary in electrical conductivity according to humidity, and thus humidity may be detected with high sensitivity.

Hereinafter, a method of fabricating a metal material wire will be described with reference to FIGS. 9 to 13. However, the descriptions of the operations that are the same as or similar to those of the embodiment described above and thus are apparent may be omitted.

Figure 9:
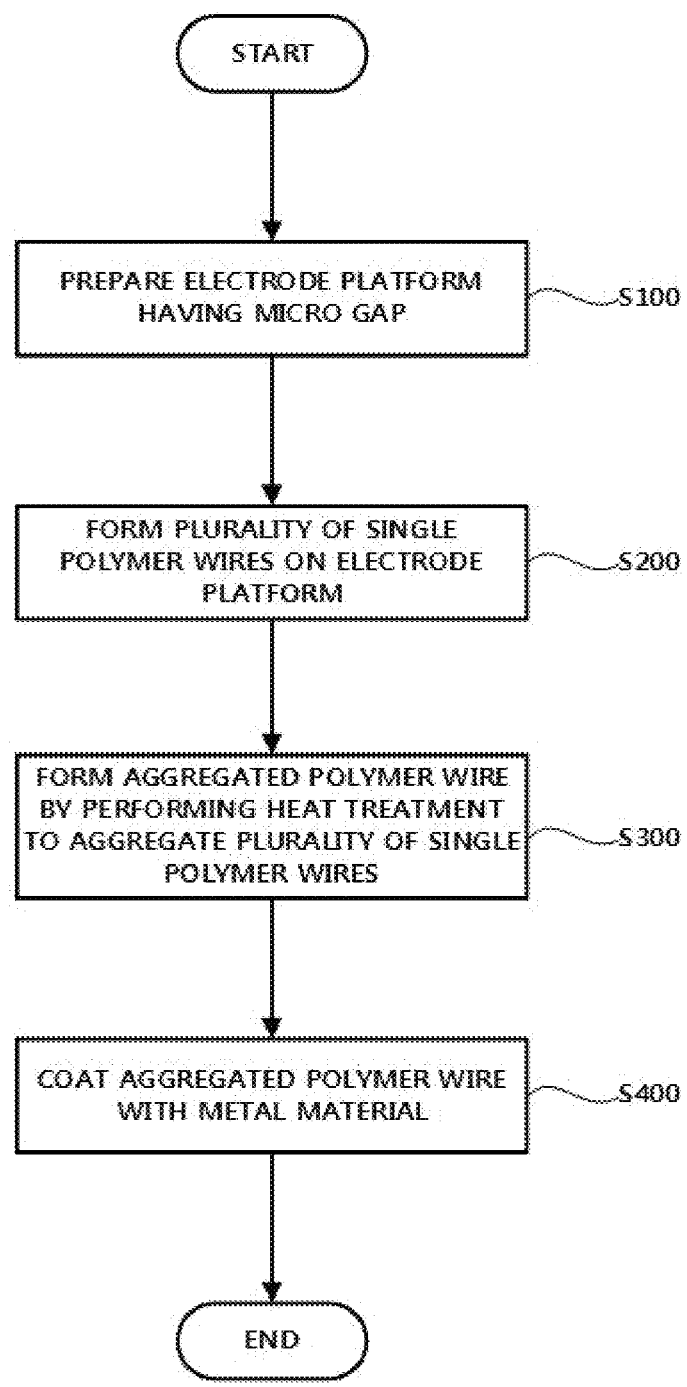
FIG. 9 is a flowchart schematically illustrating a method of fabricating a metal material wire according to the present embodiment.

FIG. 9 is a flowchart schematically illustrating a method of fabricating a wire including a metal material 400 according to the present embodiment. Referring to FIG. 9, the method of fabricating the metal wires according to the present embodiment includes preparing an electrode platform having a micro gap (S100), forming a plurality of single polymer wires on the electrode platform (S200), a heat treatment operation of forming an aggregated polymer wire by aggregating the plurality of single polymer wires (S300), and coating the aggregated polymer wire with the metal material 400 (S400).

As an example, after performing the coating with the metal material 400, an aggregated polymer wire 300 may be removed to form a wire having the metal material 400.

The operations S100 to S300 are similar to the operation of forming the aggregated polymer wire 300, and thus the description thereof is omitted. In one embodiment, after the forming of the aggregated polymer wire by performing the heat treatment (S300), adjusting the diameter of the aggregated polymer wire 300 may be further performed. As an example, in the adjusting of the diameter of the aggregated polymer wire 300, reactive ion etching (RIE) may be performed such that the diameter of the aggregated polymer wire 300 is reduced. As another example, adjusting the diameter of the aggregated polymer wire 300 may be further performed. As an example, in the adjusting of the diameter of the aggregated polymer wire 300, wet etching may be performed such that the diameter of the aggregated polymer wire 300 is reduced.

Since the reducing of the diameter of the aggregated polymer wire 300 is performed, single polymer wires 200 located on a surface of an electrode 110 may be removed. In addition, the diameter of branches 310 formed on the outer periphery of a tip 130 may be reduced.

Figure 10A:
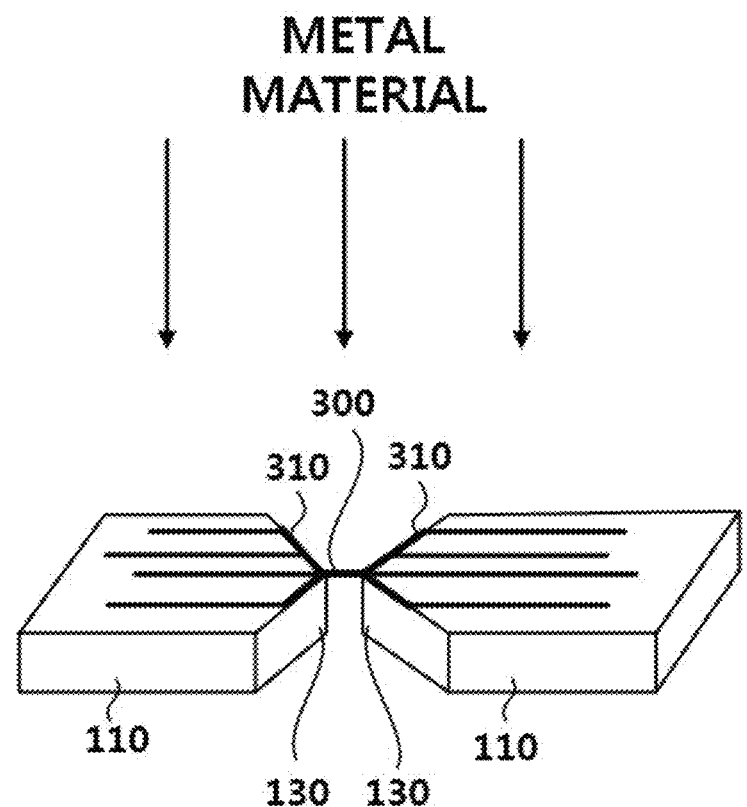
FIG. 10A is a view illustrating an example of coating an aggregated polymer wire with a metal material.
Figure 10B:
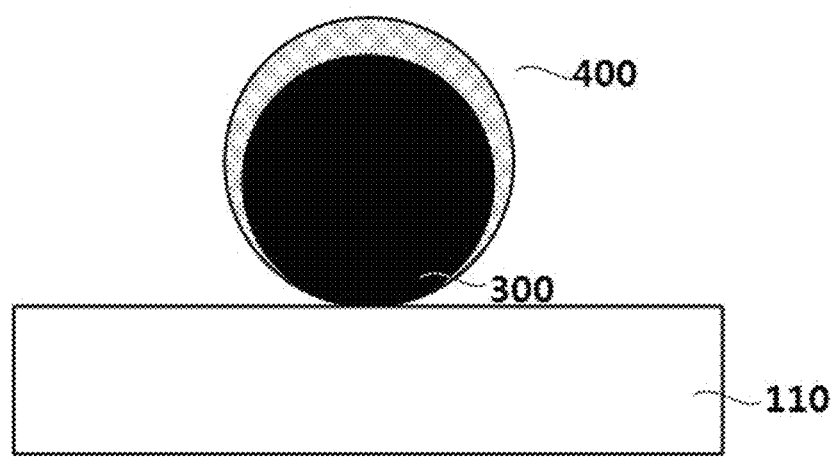
FIG. 10B is a view schematically illustrating a cross section of the aggregated polymer wire coated with the metal material in the embodiment illustrated with reference to FIG. 10A.

The aggregated polymer wire 300 is coated with the metal material 400 (S400). In the present embodiment, the term "coating" refers to a case of forming a metal material on an entire exposed surface of the aggregated polymer wire 300 as well as forming a metal material on some of the exposed surface of the aggregated polymer wire 300. FIG. 10A is a view illustrating an example of coating the aggregated polymer wire 300 with the metal material 400, and FIG. 10B is a view schematically illustrating a cross section of the aggregated polymer wire 300 coated with the metal material 400 in the embodiment illustrated with reference to FIG. 10A. Referring to FIG. 10A, the metal material 400 may be provided from directly above the surface of the electrode 110 to coat the aggregated polymer wire 300. Although not illustrated in the drawing, the aggregated polymer wire 300 may be coated with the metal material 400 using a shadow mask configured to open a desired region.

The metal material formed on the surface of the electrode 110 in the coating process may function as an electrode, and the metal wire and the electrode are simultaneously formed so that a separate contact resistance does not occur.

When the metal material 400 is provided from directly above the electrode 110 to coat the aggregated polymer wire 300 as illustrated in FIG. 10A, the metal material 400 is mainly coated on an upper side of the exposed surface of the aggregated polymer wire 300 as illustrated in FIG. 10B.

Figure 11A:
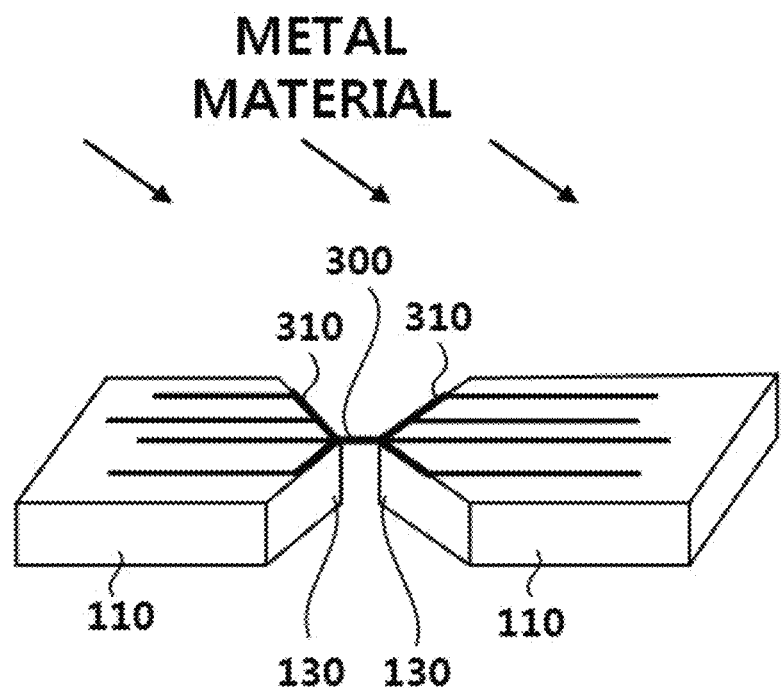
FIG. 11A is a view illustrating the case in which the metal material is provided to be inclined from above a surface of an electrode.
Figure 11B:
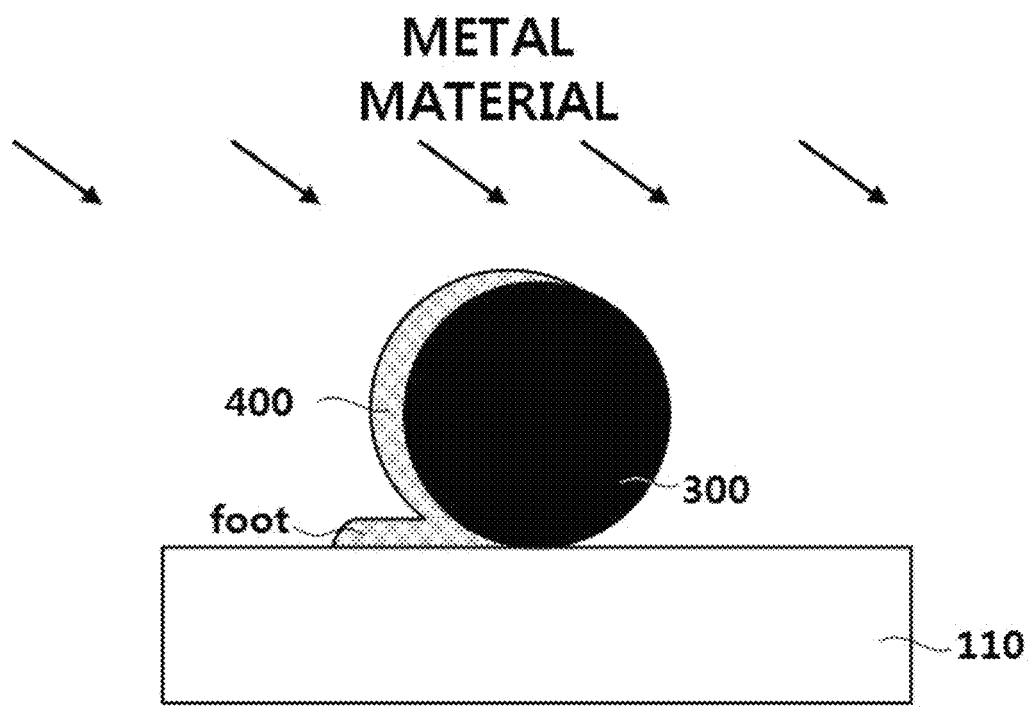
FIG. 11B is a view illustrating an example in which the metal material is coated when the metal material is provided to be inclined from above the surface of the electrode.

FIG. 11A is a view illustrating the case in which the metal material 400 is provided to be inclined from above the surface of the electrode, and FIG. 11B is a view illustrating an example in which the metal material 400 is coated when the metal material 400 is provided to be inclined from above the surface of the electrode 110. Referring to FIGS. 11A and 11B, since the metal material 400 is provided to be inclined from above the electrode 110, the portion of the aggregated polymer wire 300 in an inclined direction is coated with the metal material 400 and the portion of the aggregated polymer wire 300 in a direction opposite to the inclined direction is exposed.

Further, a foot of the metal material 400 is formed in the inclined direction. The adhesion between the metal material 400 and the surface of the electrode 110 is enhanced due to the foot of the metal material 400, thereby preventing the metal material 400 from being separated from the surface of the electrode 110 in the subsequent operation of removing the aggregated polymer wire 300 (S500).

In the embodiment in which the metal material 400 is provided to be inclined from above the surface of the electrode, an electrode platform 100 on which the aggregated polymer wire 300 is formed is positioned to be inclined by as much as the desired angle in normal deposition equipment, and the aggregated polymer wire 300 is coated with the metal material 400.

In the embodiments described above, the aggregated polymer wire 300 may be coated with the metal material 400 using an evaporation method. The metal material 400 is not particularly limited as long as it is a material that can be deposited. For example, the metal material may include at least one or more selected from the group consisting of silver (Ag), aluminum (Al), gold (Au), palladium (Pd), copper (Cu), iron (Fe), nickel (Ni), chromium (Cr), magnesium (Mg), manganese (Mn), molybdenum (Mo), phosphorus (P), lead (Pb), platinum (Pt), ruthenium (Ru), titanium (Ti), tungsten (W), zinc (Zn), and oxides thereof. In addition, e-beam evaporation, thermal evaporation, sputtering, and the like may be used as the evaporation method.

In another example, the metal material 400 may include nanoparticles, carbon nantotubes (CNTs) and graphene. In an example, the aggregated polymer wire 300 may be coated with nanoparticles such that the coated nanoparticles are connected to each other. Dip coating or drop coating can be performed in order to coat the nanoparticles onto the aggregated polymer wire 300. In a further example, carbon nanotubes (CNTs) or graphene is coated to the aggregated polymer wire by the dip coating or the drop coating.

In a sensor including the wire according to the present embodiment, the surface of the electrode 110 may be coated with the metal material 400. The metal material 400 may react with target gas to be detected by the sensor, and the electrical properties of the metal material 400 may change as a result of the reaction. However, as described above, by forming a metal film having good electrical conductivity on the surface of the electrode 110, relatively insensitive changes in electrical properties due to the reaction between the metal material 400 formed on the surface of the electrode 110 and the detection target may be eliminated, and it may be limited to the electrical properties generated in the nanowires in which the reaction is sensitive.

In one embodiment, the aggregated polymer wire 300 may be coated with a metal material, and the aggregated polymer wire 300 may be removed to form a metal material wire. FIG. 12 is a cross-sectional view schematically illustrating the state in which the aggregated polymer wire 300 is removed from the aggregated polymer wire coated with the metal material 400. Referring to FIG. 12, since the aggregated polymer wire 300 is removed, only a metal material wire 500 may remain between the electrode 110 and the electrode 110.

FIG. 13 is a cross-sectional view illustrating the state in which a drying process is performed after the aggregated polymer wire is removed from the aggregated polymer wire coated with the metal material 400. Referring to FIG. 13, as the metal material 400 is dried, the metal material wire 500 is connected between the tips 130 of the electrodes.

In one embodiment, the method of removing the aggregated polymer wire may include a method of immersing a polymer nanowire coated with a metal material in a solvent. Any solvent may be used without particular limitation as the solvent as long as it can remove polymer nanowires and does not cause damage to the coated metal material and a microelectromechanical systems (MEMS) platform. For example, a chloroform solution, an acetone solution, dimethylformamide, purified water, or the like may be used as the solvent.

In one embodiment, when the thickness of the metal material 400 coated on the aggregated polymer wire is in a range of about 5 nm to 20 nm, the metal material wire is formed as a metal material wire having a small diameter. On the other hand, when the coated metal material has a thickness of about 30 nm or more, the metal material wire 500 is formed as a shell-shaped wire having the shape of the aggregated polymer wire.

In addition, the polymer nanowire 300 fabricated according to the fabrication method of the present disclosure may be coated with other nanoparticles. The polymer nanowire coated with the nanoparticles as described above may be used in a gas sensor or the like.

Hereinafter, the metal material wire 500 according to the present embodiment will be described with reference to FIG. 13. As shown in FIG. 13, the metal material wire 500 may be formed between the tips 130 of the electrodes, which are spaced apart from each other, and may be made of a metal material or a polymer.

The metal material wire 500 may detect gas and may change in electrical properties such as electrical resistance, resistivity, and the like. Using these characteristics, the metal material wire 500 may be utilized as a gas sensor. In one embodiment, when the metal material wire 500 is made of palladium (Pd), hydrogen ($H_2$) gas may be detected, and when the metal material wire 500 is made of $SnO_2$ or $WO_3$, volatile organic compounds (VOCs) such as $NO_x$, xylene, toluene, benzene, and the like may be detected.

Figure 14:
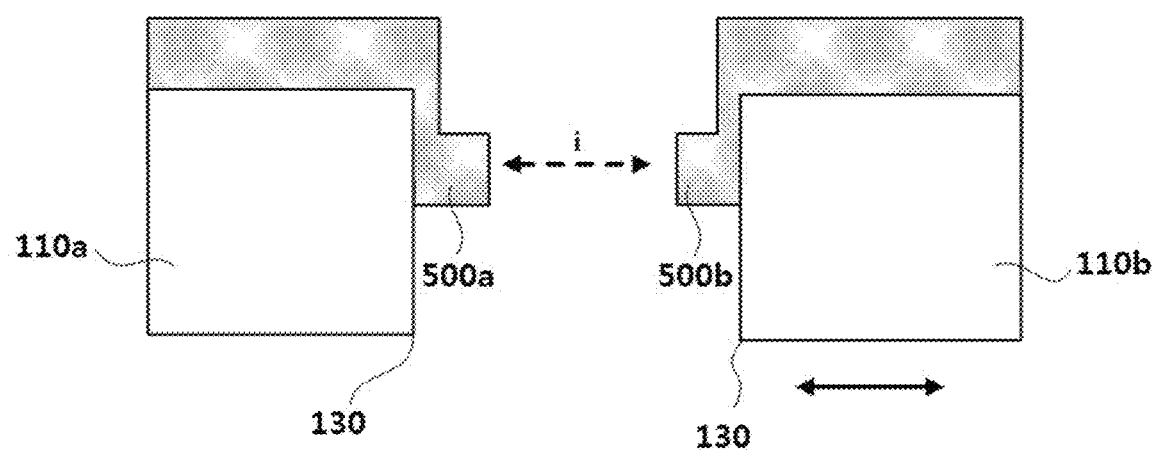
FIG. 14 is an enlarged cross-sectional view schematically illustrating a portion of a sensor according to the present embodiment.

FIG. 14 is an enlarged cross-sectional view schematically illustrating a portion of a sensor according to the present embodiment. Referring to FIG. 14, the sensor includes electrodes 110a and 110b each having a protruding tip 130, and wire segments 500a and 500b located on surfaces of the two electrodes 110a and 110b, respectively, and extending through the protruding tip 130.

In the illustrated embodiment, the electrode 110a is fixed, but the electrode 110b is movable. Accordingly, as the electrode platform including the electrodes 110a and 110b moves, the distance between the wire segments 500a and 500b changes. Accordingly, the electrical properties between the wire segments may change, and a current i and/or a voltage varying in magnitude may be formed when a bias is provided. Thus, the movement may be detected by detecting the current i and/or the voltage.

As an example, the wire segments 500a and 500b may be formed by forming the aggregated polymer wire 300, the metal material wire 500, and the aggregated polymer wire coated with the metal material, which are described above, and then cutting the wires. As an example, the process of forming the wire segments may be performed by irradiating a focused ion beam (FIB) onto the wire 500.

Experimental Examples

Figure 15A:
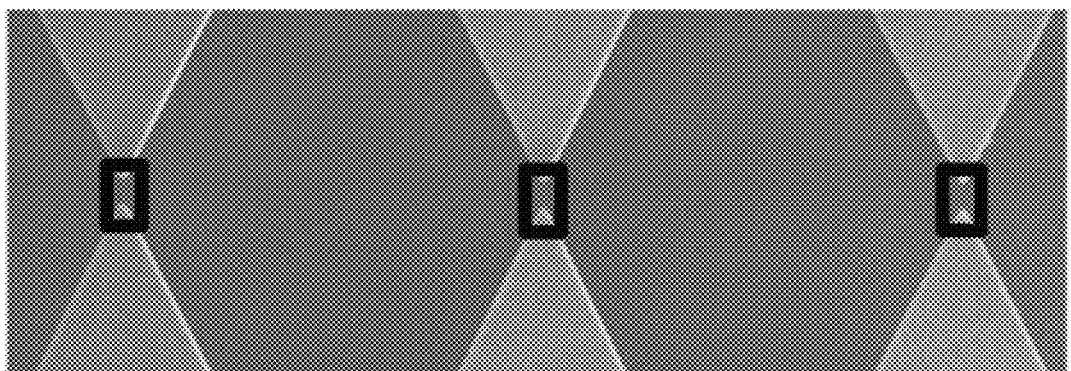
FIGS. 15A to 15C are microscope images of palladium (Pd) wires formed according to the present embodiment.
Figure 15B:
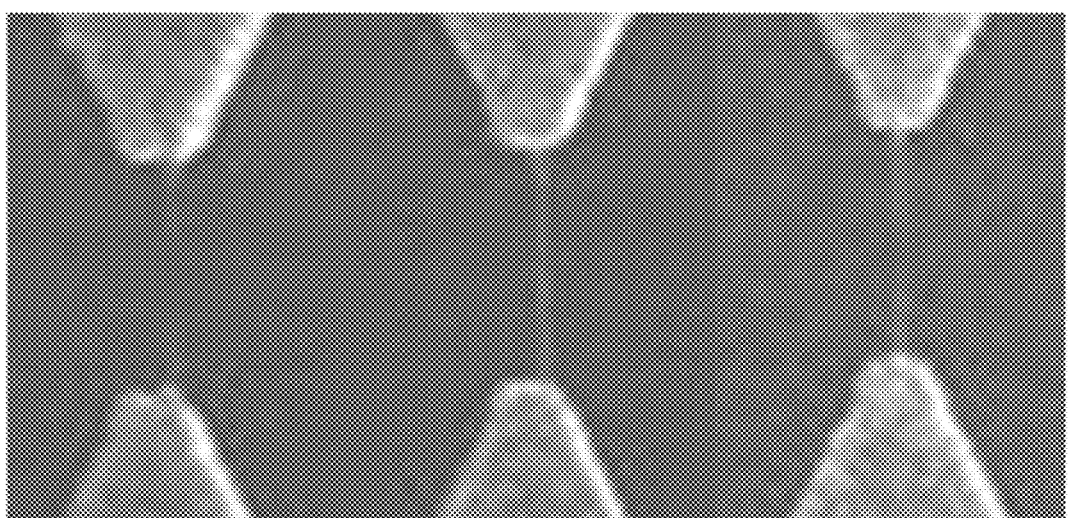
Figure 15C:
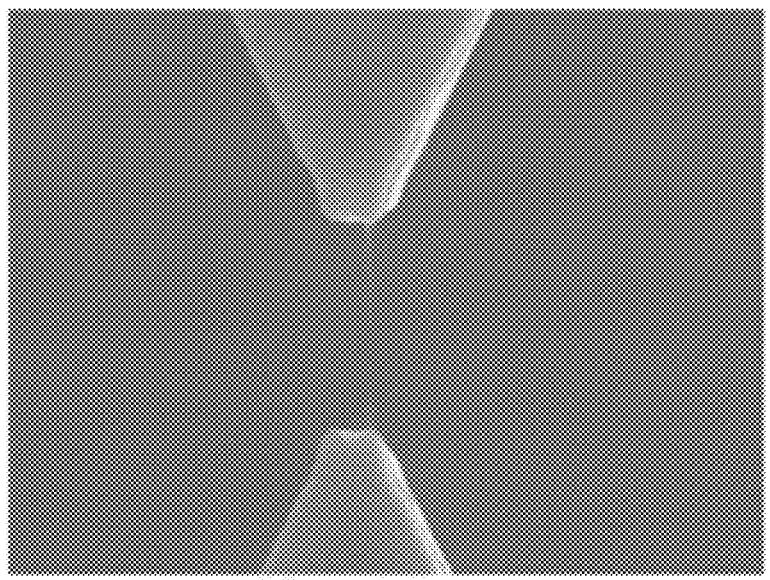

FIGS. 15A to 15C are microscope images of palladium (Pd) wires formed according to the present embodiment, FIG. 15B is an enlarged view of portions illustrated by rectangles in FIG. 15A, and FIG. 15C is an enlarged view of one of the illustrated palladium wires. Referring to FIGS. 15A to 15C, it was possible to form a plurality of palladium wires having a diameter of less than 100 nm by performing a batch process as in the embodiment of the present disclosure, and the yield was 88%.

The palladium wire illustrated in FIG. 15 may be used as a gas sensor for sensing hydrogen gas. When palladium is exposed to hydrogen, the palladium reacts with the hydrogen, and is changed to $PdH_x$ and changes in electrical resistance. Accordingly, the palladium wire may be used as a gas sensor for sensing hydrogen gas with high sensitivity.

FIG. 16 is a graph illustrating the results of detecting hydrogen gas by a sensor using the palladium wire according to the present embodiment. Referring to FIG. 16, it can be seen that when hydrogen gas of 1000 ppm is supplied while a bias voltage of 1 V is applied, an electrical resistance of the palladium wire is increased by 1.25 times compared to the case in which the hydrogen gas is not provided. Accordingly, the hydrogen gas may be detected by detecting a change in resistance and a change in current or voltage generated accordingly.

Figure 17:
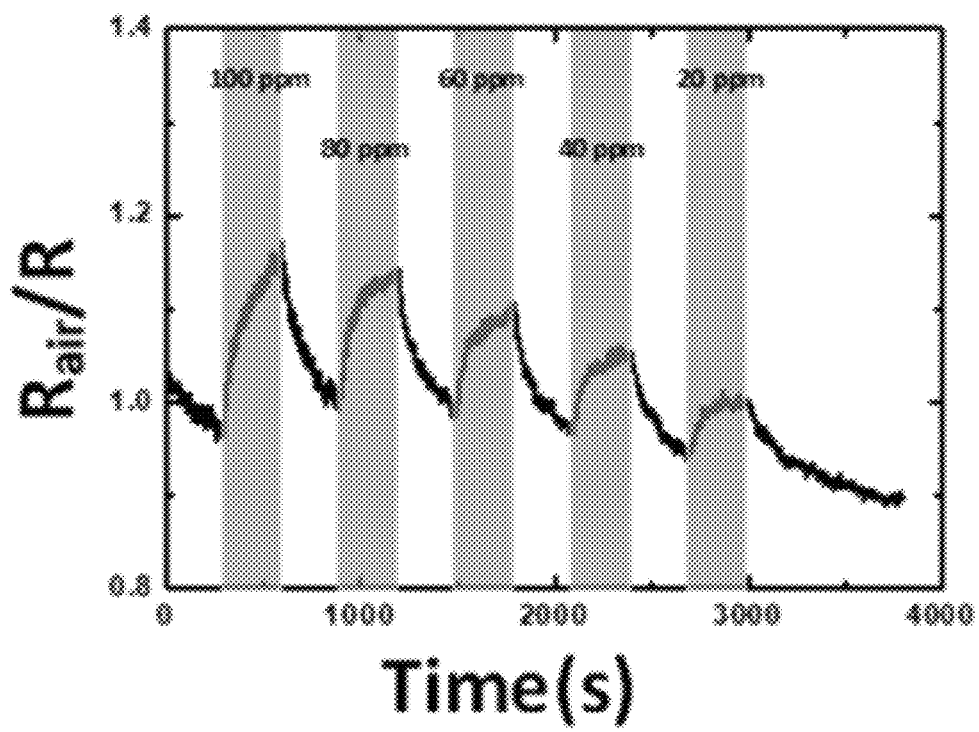
FIG. 17 is a graph illustrating the results of detecting nitrogen dioxide ($NO_2$), which is a kind of volatile organic compound (VOC), by a sensor using tin dioxide according to the present embodiment.

FIG. 17 is a graph illustrating the results of detecting nitrogen dioxide ($NO_2$), which is a kind of VOC, by a sensor using tin dioxide ($SnO_2$) according to the present embodiment, and a bias voltage of 2 V is provided. Concentrations of the nitrogen dioxide are 100 ppm, 80 ppm, 60 ppm, 40 ppm, and 20 ppm from the leftmost side. From the results illustrated, it can be seen that, in the sensor according to the present embodiment, the ratio of electrical resistance changes more in the case in which nitrogen dioxide gas, which is the target gas, is provided compared to the case in which the nitrogen dioxide gas is not provided. Accordingly, based on this, nitrogen dioxide gas having a low concentration of 20 ppm may be detected.

According to the present disclosure, the positions in which nanowires are formed can be controlled, the number of the wires to be formed can be adjusted, and the nanowires can be formed in a large area and in a large amount by performing a batch process.

Although the embodiments of the present disclosure have been described in detail above with reference to the accompanying drawings, this is merely an example for implementation, and those skilled in the art will understand that various modifications and other equivalent embodiments are possible therefrom. Accordingly, the true technical scope of the present disclosure should be determined only by the appended claims.

What is claimed is:

1. A method of fabricating a polymer wire, the method comprising:
   preparing an electrode platform having a micro gap;
   forming a plurality of single polymer wires on the electrode platform; and
   a heat treatment operation of aggregating the plurality of single polymer wires to form an aggregated polymer wire,
   wherein the heat treatment operation comprises:
   heating the plurality of single polymer wires to a glass transition temperature of the plurality of single polymer wires such that the plurality of single polymer wires moves and aggregates to a single polymer wire.

2. The method of claim 1, wherein
   the electrode platform includes a plurality of electrodes,
   each of the plurality of electrodes has a protruding tip, and
   a distance between the protruding tips forms the micro gap.

3. The method of claim 1, wherein the micro gap is in a range of one hundred nanometers to several hundred micrometers.

4. The method of claim 1, wherein the single polymer wire has a diameter of 100 nm to 1000 nm.

5. The method of claim 1, wherein the forming of the plurality of single polymer wires is performed using a solution containing at least one selected from the group consisting of polyethylene oxide, polyurethane, polyethylene, polypropylene, polystyrene, polyvinyl chloride, and polybutadiene.

6. The method of claim 5, wherein the forming of the plurality of single polymer wires is performed by electrospinning or transferring.

7. The method of claim 1, wherein the heat treatment is performed by exposing the formed single polymer wires to a temperature of 50° C. to 200° C.

8. A method of fabricating a metal material wire, the method comprising:
   preparing an electrode platform having a micro gap;
   forming a plurality of single polymer wires on the electrode platform;
   a heat treatment operation of aggregating the plurality of single polymer wires to form an aggregated polymer wire; and
   coating the aggregated polymer wire with a metal material,
   wherein the heat treatment operation comprises:
   heating the plurality of single polymer wires to a glass transition temperature of the plurality of single polymer wires such that the plurality of single polymer wires moves and aggregates to a single polymer wire.

9. The method of claim 8, further comprising removing the aggregated polymer wire to form the metal material wire.

10. The method of claim 9, wherein the removing of the aggregated polymer wire is performed by removing the aggregated polymer wire coated with the metal material by wet etching or reactive ion etching (RIE).

11. The method of claim 10, wherein the wet etching is performed by immersing the aggregated polymer wire coated with the metal material in one etchant selected from the group consisting of a chloroform solution, an acetone solution, dimethylformamide, and purified water.

12. The method of claim 8, wherein the metal material includes at least one or more selected from the group consisting of silver (Ag), aluminum (Al), gold (Au), palladium (Pd), copper (Cu), iron (Fe), nickel (Ni), chromium (Cr), magnesium (Mg), manganese (Mn), molybdenum (Mo), phosphorus (P), lead (Pb), platinum (Pt), ruthenium (Ru), titanium (Ti), tungsten (W), zinc (Zn), and oxides thereof.

13. The method of claim 12, wherein
the coating of the aggregated polymer wire with the metal material is performed by depositing the metal material on the aggregated polymer wire, and
the depositing is performed by depositing the metal material on the electrode platform in an inclined direction such that a foot of the metal material is formed on the metal material wire.

14. The method of claim 8, wherein the metal material is one of a carbon nanotubes (CNTs), graphene and nanoparticles.

15. The method of claim 8, wherein reducing a diameter of the aggregated polymer wire by reactive ion etching (RIE) is further performed prior to the coating.

* * * * *